(12) United States Patent
Hogsett et al.

(10) Patent No.: US 10,925,985 B2
(45) Date of Patent: Feb. 23, 2021

(54) SYSTEMS AND METHODS FOR STERILIZATION USING NONTHERMAL PLASMA GENERATION

(71) Applicant: Illinois Tool Works Inc., Glenview, IL (US)

(72) Inventors: Mark Edward Hogsett, Wilmington, NC (US); Steven Bernard Heymann, Los Gatos, CA (US); Carl Newberg, Tuscon, AZ (US)

(73) Assignee: Illinois Tool Works Inc., Glenview, IL (US)

( * ) Notice: Subject to any disclaimer, the term of this patent is extended or adjusted under 35 U.S.C. 154(b) by 51 days.

(21) Appl. No.: 16/204,567

(22) Filed: Nov. 29, 2018

(65) Prior Publication Data
US 2019/0160191 A1    May 30, 2019

Related U.S. Application Data

(60) Provisional application No. 62/592,785, filed on Nov. 30, 2017.

(51) Int. Cl.
*B01J 19/08*      (2006.01)
*B23H 3/02*       (2006.01)
(Continued)

(52) U.S. Cl.
CPC .................. *A61L 2/14* (2013.01); *A61L 2/24* (2013.01); *A61L 2/26* (2013.01); *A61L 9/22* (2013.01);
(Continued)

(58) Field of Classification Search
CPC ........ A61L 9/16; A61L 9/22; A61L 2209/212; A61L 2202/25; A61L 2/26;
(Continued)

(56) References Cited

U.S. PATENT DOCUMENTS 3,383,163 A    5/1968  Menashi
4,901,194 A *  2/1990  Steinman ................ H01T 23/00
                                                    250/423 R
(Continued)

OTHER PUBLICATIONS

Cleanroom Ionization for Life Science Manufacturers, Ionization Solutions, Simco-Ion Technology Group, www.simco-ion.com, ©2017 (4 pgs).

(Continued)

*Primary Examiner* — Monzer R Chorbaji
(74) *Attorney, Agent, or Firm* — McAndrews, Held & Malloy, Ltd.

(57) ABSTRACT

Systems and methods for sterilization using nonthermal plasma (NTP) ionization are disclosed. An example method for inactivation of viable microorganisms includes: inactivating viable microorganisms in a predetermined volume by: installing a plurality of ceiling mounted direct current (DC) or alternating current (AC), bipolar or steady-state, ion emitter modules based on a geometry of the predetermined volume; and producing, using the plurality of ceiling mounted ion emitter modules, a DC or AC, bipolar or steady-state, nonthermal plasma (NTP), each of the ceiling mounted ion emitter modules comprising a high voltage power supply (HVPS).

10 Claims, 3 Drawing Sheets

(51) Int. Cl.
  *B23H 7/14* (2006.01)
  *C25B 11/00* (2021.01)
  *A61L 2/14* (2006.01)
  *A61L 2/26* (2006.01)
  *H01T 23/00* (2006.01)
  *A61L 9/22* (2006.01)
  *A61L 2/24* (2006.01)

(52) U.S. Cl.
  CPC ........... *H01T 23/00* (2013.01); *A61L 2202/11* (2013.01); *A61L 2202/14* (2013.01); *A61L 2202/25* (2013.01); *A61L 2209/111* (2013.01); *H05H 2245/1225* (2013.01)

(58) Field of Classification Search
  CPC .......... A61L 2202/11; A61L 2/14; A61L 2/24; A61L 2202/14; H05H 1/24
  USPC ........ 422/32, 186.04, 306; 204/228.1, 229.4, 204/230.2, 280, 286.1
  See application file for complete search history.

(56) References Cited

U.S. PATENT DOCUMENTS

| | | | |
|---|---|---|---|
| 6,252,756 | B1 | 6/2001 | Richie, Jr. |
| 8,334,422 | B2 | 12/2012 | Gutsol |
| 8,861,166 | B2 * | 10/2014 | Richie, Jr. ............... H01T 23/00 361/213 |
| 9,452,099 | B2 | 9/2016 | Schneider |
| 10,299,882 | B2 | 5/2019 | Armour |
| 2013/0330229 | A1 | 12/2013 | Fridman |
| 2016/0051713 | A1 * | 2/2016 | Robert ...................... A61L 2/14 361/231 |

OTHER PUBLICATIONS

Int'l Search Report and Written Opinion Appln No. PCT/US2018/063253 dated May 16, 2019.

Danil Dobrynin, Inactivation of bacteria using dc corona discharge: role of ions and humidity, http://www.ncbi.nlm.nih.gov/pmc/articles/PMC3295596, Jan. 26, 2017, pp. 1-9.

GPS—300, Ceiling Cassette Air Purification System, Produce Data Sheet, www.globalplasmasolutions.com, 2020.

J. W. Arnold, et al., Use of Negative Air Ionization for Reducing Bacterial Pathogens and Spores on Stainless Steel Surfaces, ©2004 Poultry Science Association, Inc., JAPR: Research Report, pp. 200-206.

Mercedes Lopez, et al., A Review of Non-thermal Atmospheric Plasma for Food Preservation: Mode of Action, Determinants of Effectiveness, and Applications, Frontiers in Microbiology, www.frontiersin.org, Apr. 2, 2019, vol. 10, Article 622.

Puligundla Pradeep and Mok Chulkyoon, Review Paper, Non-thermal Plasmas (NTPs) for inactivation of viruses in abiotic environment, Res. J. Biotech., vol. 11(6), Jun. 2016, pp. 91-96.

Shimizu K, Komuro Y, Tatematsu S, Blajan M (Sep. 24, 2011) Study of Sterilization and Disinfection in Room Air by Using Atmospheric Microplasma. Pharm Anal Acta S1:001. doi: 10.4172/2153-2435.S1-001.

* cited by examiner

SYSTEMS AND METHODS FOR STERILIZATION USING NONTHERMAL PLASMA GENERATION

RELATED APPLICATIONS

This patent claims priority to U.S. Provisional Patent Application Ser. No. 62/592,785, filed Nov. 30, 2017, entitled "Systems and Methods for Sterilization Using Nonthermal Plasma Ionization." The entirety of U.S. Provisional Patent Application Ser. No. 62/592,785 is incorporated herein by reference.

BACKGROUND

The present disclosure relates to sterilization and, more particularly, to systems and methods for sterilization using nonthermal plasma ionization.

Due to the historic prevalence of disease/infection transmission in medical related environments, including medical device and/or pharmaceutical manufacturing, techniques have been sought and implemented which address a reduction/elimination of transmission. Transmission reduction has been accomplished for specific enclosed tasks (e.g., autoclave replacement), but not for the general environment in which a substantial quantity of viruses, bacteria, and/or spores are being collected and redistributed (i.e., transmitted).

SUMMARY

Methods and systems are provided for sterilization using nonthermal plasma generation (ionization), substantially as illustrated by and described in connection with at least one of the figures, as set forth more completely in the claims.

BRIEF DESCRIPTION OF THE DRAWINGS

These and/or other aspects will become apparent and more readily appreciated from the following description of the exemplary embodiments, taken in conjunction with the accompanying drawings.

The figures are not necessarily to scale. Where appropriate, similar or identical reference numbers are used to refer to similar or identical components.

DETAILED DESCRIPTION

Figure 1:
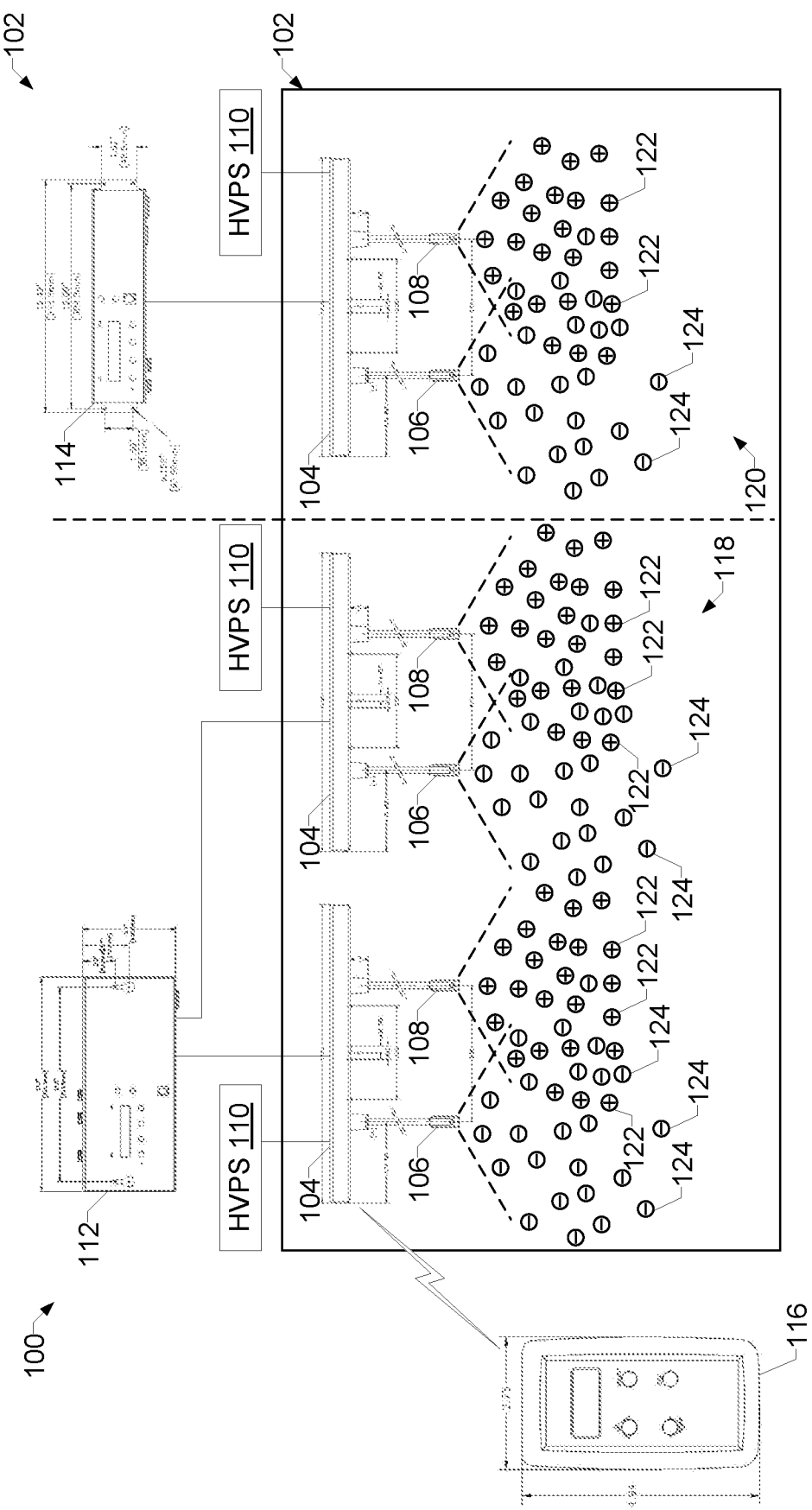
FIG. 1 illustrates a schematic diagram of an example nonthermal plasma sterilization system, in accordance with aspects of this disclosure.

Disclosed example methods and systems typically address medical operating areas, laboratory, pharmaceutical or medical device manufacturing spaces comprehensively by destroying infectious organisms in place continuously both on surfaces and airborne. In particular, disclosed example methods, and systems sterilized and/or disinfect viruses, bacteria, and spores, which are attached to airborne particles, whether aerosol droplets, airborne molecular contaminants, or large particles generated by human activity in the local environment, continuously and/or in real-time with nonthermal plasma (NTP).

In some examples, an NTP-generating system is installed onto the ceiling of pre-existing structures or designed into facilities in the planning stages. Disclosed example systems are modular, reducing the difficulty retrofitting established facilities. Such disclosed systems are referred to as ceiling ionization systems, ceiling-based ionization systems, and/or room ionization systems.

Disclosed example systems include comprehensive digital NTP generation control and monitoring using computer-based software for either standalone PCs or VM (Virtual Machine) installation. In some examples, remote hand-held programming units using wireless (e.g., infrared) increase system programming and maintenance capabilities.

Disclosed example methods for inactivation of viable microorganisms include inactivating viable microorganisms in a predetermined volume by: installing a plurality of ceiling mounted direct current (DC) or alternating current (AC), bipolar or steady-state, ion emitter modules based on a geometry of the predetermined volume; and producing, using the plurality of ceiling mounted ion emitter modules, a DC or AC, bipolar or steady-state, nonthermal plasma (NTP), each of the ceiling mounted ion emitter modules comprising a high voltage power supply (HVPS).

In some examples, the installing of the plurality of ceiling mounted ion emitter modules involves arranging the plurality of ceiling mounted ion emitter modules to have a module density in the predetermined volume based on a target ion density. In some such examples, the target ion density corresponds to a subvolume within the predetermined volume. In some examples, the installing of the plurality of ceiling mounted ion emitter modules involves providing the ceiling mounted ion emitter modules with stainless steel shrouds to protect emitters of the ceiling mounted ion emitter modules Some example methods further involve connecting the plurality of ceiling mounted ion emitter modules to a controller module and controlling the plurality of ceiling mounted ion emitter modules using the controller module. In some examples, the producing of the nonthermal plasma involves controlling at least a portion of the plurality of ceiling mounted ion emitter modules to generate the nonthermal plasma in at least one of a pulsed DC mode, a steady-state DC mode, or an AC mode.

In some example methods, the producing of the nonthermal plasma involves generating a nonthermal plasma having an alternating polarity. In some examples, the producing of the nonthermal plasma involves generating the nonthermal plasma at different plasma densities using different ones of the plurality of ceiling mounted ion emitter modules. In some examples, the producing of the nonthermal plasma further involves causing the nonthermal plasma to traverse the predetermined volume.

In some example methods, the producing of the nonthermal plasma involves deactivating of bacteria, spores, fungi, and viruses present in the predetermined space in at least respective threshold fractions of the bacteria, spores, fungi, and viruses. In some examples, the producing of the nonthermal plasma involves producing a neutral net charge.

FIG. 1 illustrates a schematic diagram of an example nonthermal plasma sterilization system 100. The example system 100 of FIG. 1 may be used to provide sterilization of an entire room 102 from microorganisms such as bacteria, spores, fungi, and/or viruses, whether airborne or surface-borne. The example system 100 is modular and can be installed into a new room and/or to retrofit an existing room of any size or configuration.

The example system 100 includes one or more ceiling-mounted ion emitter modules 104, which can be of either AC or DC type and/or operate in bipolar or steady-state modes. The modules 104 may be mounted in any desired configuration, such as a spaced grid. The density and arrangement of modules 104 within a grid placement may be based on a desired level of ion coverage (e.g., a required ion density to achieve a particular sterilization level).

Each of the example ion emitter modules 104 of FIG. 1 produces a DC or AC, bipolar or steady-state, nonthermal plasma (NTP) via two separate emitters 106, 108 powered by individual DC or AC high voltage power supplies (HVPS) 110. The HVPS 110 may provide the same or different emitter outputs to each of the ion emitter modules 104. In some examples, the HVPS 110 provides voltages between 0 to 20 kVDC and currents between 0 to 2 μA. The example HVPS 110 may be powered with low voltage (e.g., 24 VAC or VDC) wiring.

The example ion emitter modules 104, of either AC or DC type, are operated using variable pulsed intervals or steady-state and/or using varying power settings to generate a large and expanding NTP. The DC or AC, bipolar or steady-state, NTP generated by the ion emitter modules 104 expands to fill the enclosed room 102 with an alternating polarity NTP. The example ion emitter modules 104 may be operated using plasma production modes such as pulsed DC, steady-state DC, standby, and/or any combination of modes. The ion emitter modules 104 are constructed with materials exhibiting high resistance to disinfection chemical treatments commonly applied to controlled medical, laboratory, or manufacturing spaces. Example materials include stainless steel and/or any other materials defined by industry specification.

The ion emitter modules 104 (DC or AC, bipolar or steady-state) in the system 100 are digitally controlled using one or more digital controllers 112, 114. The example digital controller 112 controls a first set of the ion emitter modules 104, and the digital controller 114 controls a second set of the ion emitter modules 104. The example digital controllers 112, 114 may differ in the number of ion emitter modules 104 that can be controlled and/or the features that can be provided. The ion emitter modules 104 are individually addressable by the controllers 112, 114. In some examples, one of the controllers 112, 114 in a multiple-controller system may be designated as a master controller.

The ion emitter modules 104 may be connected in parallel and/or daisy-chained, for power and/or control purposes. The ion emitter modules 104 are individually programmable via the digital controllers 112, 114, via a software manager program executed on a general-purpose computer, and/or via a handheld programming device. The example software manager program may, for example, display emitter pod layout maps with visual and/or system alarm mode processing and/or manage emitter pod maintenance alarms, emitter pod failures, performance degradation, and/or any other configuration and/or diagnostic information. The example controllers 112, 114 and/or the ion emitter modules 104 are accessible and/or programmable via a hand-held terminal at the location of the digital controller 112, 114 or specific emitter modules.

The example ion emitter modules 104 have wireless communication ability (e.g., infrared, WiFi, Bluetooth, NFC, Zigbee, etc.) and can be programmed individually from directly below via hand-held wireless programming devices 116. The programming devices 116 may be used to verify configurations of one or more ion emitter modules 104.

The example HVPSs 110 and/or the example controllers 112, 114 may be located within the room 102, directly adjacent the room 102 (e.g., above the ceiling), and/or in a remote location (e.g., a different room) from the ion emitter modules 104.

While the example system 100 is illustrated with three ion emitter modules 104, any number of ion emitter modules 104 and/or controllers 112, 114 may be used, based on the desired ionization coverage for a particular room and/or portion of a room. The example ceiling mounted system 100 may be configured uniformly cover an entire ceiling to floor space of the room 102 in which the system 100 is installed.

In some examples, sub-volumes 118, 120 or sub-areas of a given room can be selectively ionized to provide local targeted coverage, and/or different sub-volumes or sub-areas of the room 102 can be ionized with different ion densities. For example, the sub-volume 118 of the room 102 may have a higher density of the ion emitter modules 104 than the sub-volume 120 of the room 102. The number and/or arrangement of the ion emitter modules 104 is selected and/or determined based on the ion densities of the room 102 and/or sub-volumes of the room 102.

In operation, the ion emitter modules 104 produce a DC or AC, bipolar or steady-state, nonthermal plasma including positive ions 122 and negative ions 124 to inactivate airborne and/or surface-borne microorganisms (e.g., bacteria, spores, fungi, and/or viruses) while producing a substantially neutral net charge. The ion emitter modules 104 may produce a nonthermal plasma having an alternating polarity and/or simultaneously generating ions having both positive and negative polarities (e.g., using different electrodes).

Based on the arrangements of the ion emitter modules 104 and/or plasma production modes, the example ion emitter modules 104 may generate the nonthermal plasma at different plasma densities for different portions of the room 102. The ion emitter modules 104 generate the nonthermal plasma to cause the ions 122, 124 to traverse the entirety of the room 102 and/or at least a predetermined volume of the room 102.

Example implementations of the ion emitter modules 104 and the controllers 112, 114, are described in U.S. Pat. No. 8,861,166 to Richie, Jr., et al., and U.S. Pat. No. 4,901,194, to Steinman, et al. The entireties of U.S. Pat. Nos. 8,861,166 and 4,901,194 are incorporated herein by reference.

Figure 2:
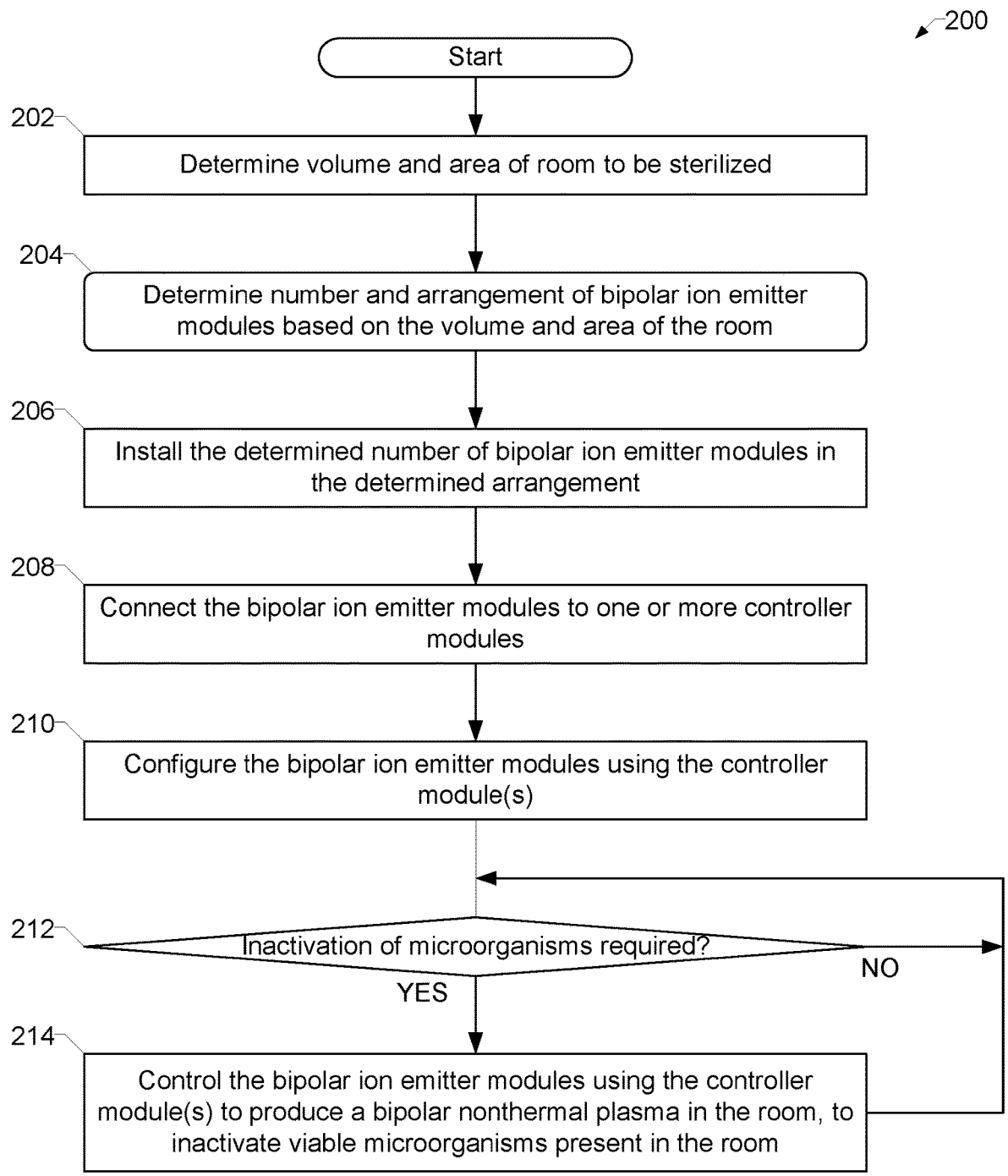
FIG. 2 is a flowchart representative of an example method to inactivate viable microorganisms using nonthermal plasma sterilization, in accordance with aspects of this disclosure.

FIG. 2 is a flowchart representative of an example method 200 to inactivate viable microorganisms using nonthermal plasma sterilization. The example method 200 is described below with reference to the example system 100 of FIG. 1.

At block 202, a volume and/or area of a room that is to be sterilized (e.g., the room 102) is determined. The sterilization may be continuous or noncontinuous, and/or different portions of the room 102 (e.g., sub-volumes 118, 120) may have different sterilization requirements. In some examples, a microorganism reduction level (e.g., a log-kill ratio) may be defined for the room 102.

At block 204, the number and arrangement of ion emitter modules are determined based on the volume and area of the room 102. For example, a number of ion emitter modules 104 needed to provide one or more ionization level(s) necessary to achieve a particular sterilization, volumetric ion coverage, and/or area ion coverage, may be determined based on the volume and/or area of the room 102, height of the room 102, airflow rate(s) within the room 102, and/or ionization capacity of the ion emitter modules 104.

At block 206, the determined number of ion emitter modules 104 are installed in the determined arrangement. For example, the ion emitter modules 104 are installed on the ceiling of the room 102 to provide the desired ionization. Installation of the ion emitter modules 104 may further involve connecting the ion emitter modules 104 to respective HVPSs 110.

At block 208, the ion emitter modules 104 are connected to one or more controller modules (e.g., the digital controllers 112, 114 of FIG. 1). For example, the ion emitter modules 104 may be coupled to the digital controllers 112, 114 via a bus, point-to-point connections, wireless connections, and/or any other connections. In some examples, a first subset of the ion emitter modules 104 are coupled to the digital controller 112, up to a control capacity of the digital controller 112. A second subset of the ion emitter modules 104 is connected to the digital controllers 114 (up to a control capacity of the digital controllers 114).

At block 210, the ion emitter modules 104 are configured using the connected controller module(s) 112, 114. For example, the ion emitter modules 104 may be configured for one or more plasma production modes (e.g., pulsed DC, steady-state DC, standby, and/or any combination of modes), a pulsing interval, and/or any other configurable aspects, at least some of which are described in U.S. Pat. Nos. 8,861,166 and 4,901,194.

At block 212, the example controller(s) 112, 114 may determine whether inactivation of microorganisms is required. In some examples, the controller(s) 112, 114 more generally determine whether ionization is to be performed, which may be based on a schedule and/or one or more sensors indicative of a sterilization level of the room 102. In some examples, inactivation of microorganisms is continuous and, thus, block 212 may be omitted.

When inactivation of microorganisms is required (block 212), at block 214 the controller(s) 112, 114 control the ion emitter modules 104 to produce a nonthermal plasma in the room 102, to inactivate viable microorganisms in the room 102. For example, the ion emitter modules 104 generate the positive ions 122 and the negative ions 124 to result in a substantially neutral charge within the room 102, while the positive ions 122 and/or the negative ions 124 inactivate airborne and/or surface-borne microorganisms.

In the example method 200, blocks 212 and 214 iterate to generate nonthermal plasma as appropriate to provide sterilization to the room 102.

Figure 3:
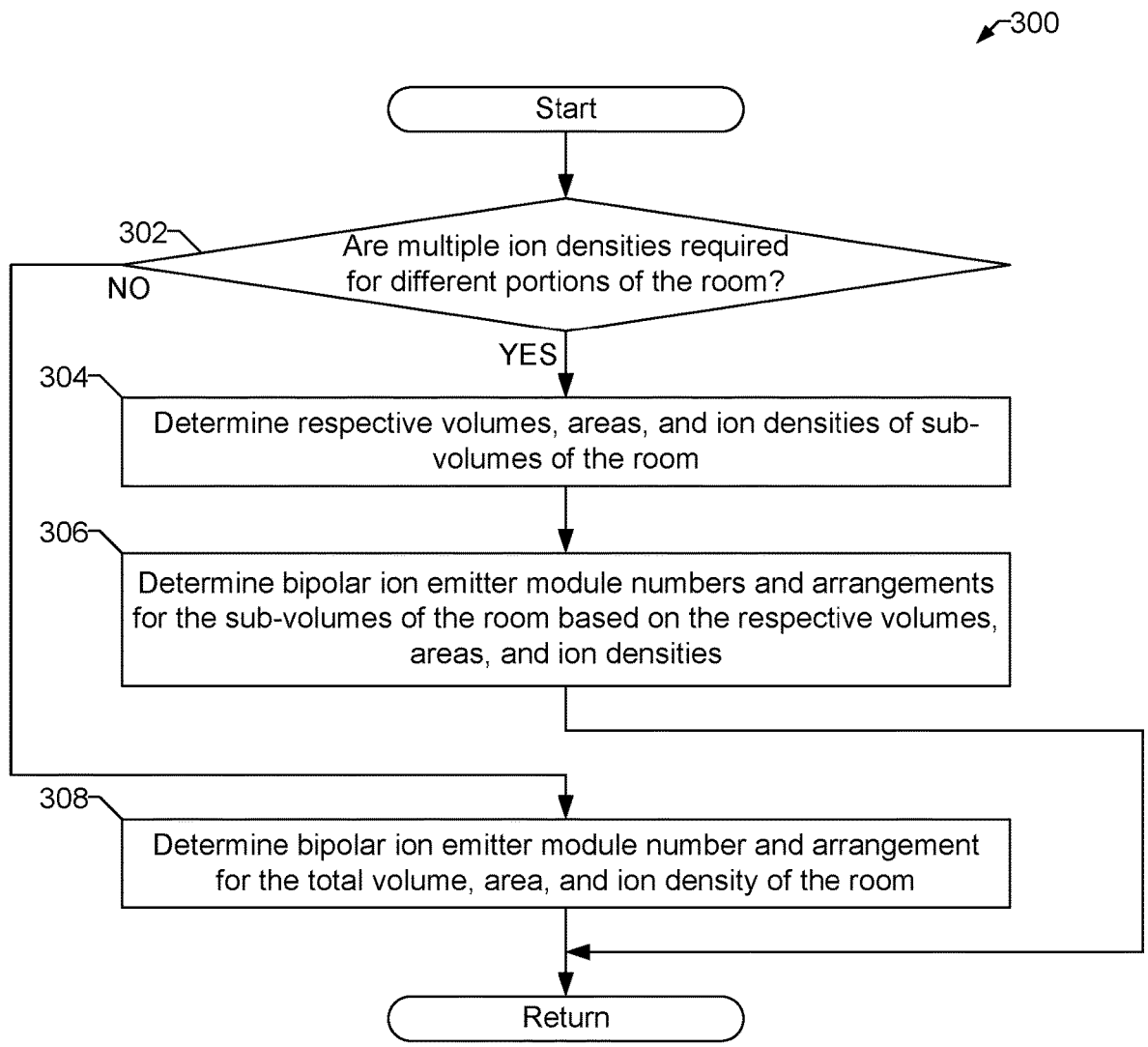
FIG. 3 show is a flowchart representative of an example method to determine a number and arrangement of DC or AC, bipolar or steady-state ion emitter modules, in accordance with aspects of this disclosure.

FIG. 3 show is a flowchart representative of an example method 300 to determine a number and arrangement of the ion emitter modules 104 of FIG. 1. The example method 300 may be performed to implement block 204 of FIG. 2, and may begin after performing block 202 of FIG. 2.

When multiple ion densities are required for different portions of a room (block 302), at block 304, respective volumes, areas, and ion densities of sub-volumes of the room 102 (e.g., sub-volumes 118, 120) are determined. At block 306, ion emitter module numbers and arrangements for the sub-volumes 118, 120 of the room 102 are determined based on the respective volumes, areas, and ion densities.

When multiple ion densities are not required for different portions of a room (e.g., a same ion density for the room 102 is acceptable) (block 302), at block 308 the ion emitter module number and arrangement are determined for the total volume, area, and ion density of the room 102.

After determining ion emitter module number(s) and arrangement(s), the example method 300 ends. The example method 200 may then resume with block 206.

The present methods and systems may be realized in hardware and/or a combination of i) hardware and ii) software and/or firmware. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system with a program or other code that, when being loaded and executed, controls the computing system such that it carries out the methods described herein. Another typical implementation may comprise one or more application specific integrated circuit or chips. Some implementations may comprise a non-transitory machine-readable (e.g., computer readable) medium (e.g., FLASH memory, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

The above-cited patents and patent publications are hereby incorporated by reference in their entirety. While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed is:

1. A method for inactivation of viable microorganisms, the method comprising:
   inactivating viable microorganisms in a predetermined volume by:
      installing a plurality of ceiling mounted direct current (DC) or alternating current (AC), bipolar or steady-state, ion emitter modules based on a geometry of the predetermined volume, wherein the installing of the plurality of ceiling mounted ion emitter modules comprises arranging the plurality of ceiling mounted ion emitter modules to have a module density in the predetermined volume based on a target ion density;

producing, using the plurality of ceiling mounted ion emitter modules, a DC or AC, bipolar or steady-state, nonthermal plasma (NTP), each of the ceiling mounted ion emitter modules comprising a high voltage power supply (HVPS);

connecting the plurality of ceiling mounted ion emitter modules to a controller module; and controlling the plurality of ceiling mounted ion emitter modules using the controller module.

2. The method as defined in claim 1, wherein the target ion density corresponds to a subvolume within the predetermined volume.

3. The method as defined in claim 1, wherein the producing of the nonthermal plasma comprises controlling at least a portion of the plurality of ceiling mounted ion emitter modules to generate the nonthermal plasma in at least one of a pulsed DC mode, a steady-state DC mode, or an AC mode.

4. The method as defined in claim 1, wherein the installing of the plurality of ceiling mounted ion emitter modules comprises providing the ceiling mounted ion emitter modules with stainless steel shrouds to protect emitters of the ceiling mounted ion emitter modules.

5. The method as defined in claim 1, wherein the producing of the nonthermal plasma comprises generating a nonthermal plasma having an alternating polarity.

6. The method as defined in claim 5, wherein the producing of the nonthermal plasma comprises generating the nonthermal plasma at different plasma densities using different ones of the plurality of ceiling mounted ion emitter modules.

7. The method as defined in claim 1, wherein the producing of the nonthermal plasma further comprises causing the nonthermal plasma to traverse the predetermined volume.

8. The method as defined in claim 1, wherein the producing of the nonthermal plasma comprises deactivating of bacteria, spores, fungi, and viruses present in the predetermined space in at least respective threshold fractions of the bacteria, spores, fungi, and viruses.

9. The method as defined in claim 1, wherein the producing of the nonthermal plasma comprises producing a neutral net charge.

10. The method as defined in claim 1, wherein the installing of the plurality of ceiling mounted ion emitter modules comprises arranging the plurality of ceiling mounted ion emitter modules based on a first target ion density for a first subvolume of the predetermined volume and a second target ion density for a second subvolume of the predetermined volume, the second target ion density being different than the first target ion density.

* * * * *